United States Patent [19]

Parker

[11] 4,335,098
[45] Jun. 15, 1982

[54] ACYLATED FURANYL AND THIENYL ACRYLIC ACIDS

[75] Inventor: Roger A. Parker, Cincinnati, Ohio

[73] Assignee: Merrell Dow Pharmaceuticals Inc., Cincinnati, Ohio

[21] Appl. No.: 267,236

[22] Filed: May 26, 1981

Related U.S. Application Data

[63] Continuation-in-part of Ser. No. 181,917, Aug. 27, 1980, abandoned.

[51] Int. Cl.$^3$ .................... A61K 31/38; A61K 31/34; C07D 307/12; C07D 333/24
[52] U.S. Cl. ................................ 424/275; 424/285; 549/71; 549/72; 549/488; 542/429
[58] Field of Search .............................. 424/275, 285; 260/347.3, 347.4, 347.5; 549/71, 72; 547/429

[56] References Cited

PUBLICATIONS

Chem Abstracts, vol. 69 (1968), p. 106358n, Fawcett.

*Primary Examiner*—Alan Siegel
*Attorney, Agent, or Firm*—Raymond A. McDonald; William J. Stein; Gary D. Street

[57] ABSTRACT

This invention relates to acylated furanyl acrylic acids, salts, esters and amides, to acylated thienyl acrylic acids, salts, esters and amides, and to their use as hypolipidemic agents, and to the processes for producing said compounds.

8 Claims, No Drawings

ACYLATED FURANYL AND THIENYL ACRYLIC ACIDS

This is a continuation-in-part of Ser. No. 181,917 filed Aug. 27, 1980, now abandoned.

This invention relates to novel compositions of matter classified in the art of chemistry as acylated furanyl and thienyl acrylic acids, esters and amides, and to the methods for making and using such compositions.

The invention sought to be patented in one of its process aspects resides in the acylation of either furan acrylate or a thiophene acrylate and subjecting the so-obtained acylated derivatives to appropriate facultative finishing steps to produce the desired compounds of this invention.

In another of its process aspects of this invention relates to the use of the compounds of this invention as hypolipidemic agents useful in the treatment of cardiovascular disease states wherein high blood lipids are usually implicated.

The invention in one of its composition of matter aspects relates to acylated thiophene acrylates or furan acrylates in admixture with a pharmaceutically acceptable carrier suitable for enteral or parenteral administration.

More particularly, this invention relates to the novel compositions of matter having the general structural formula

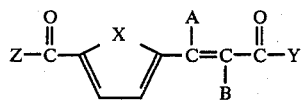   I and the pharmaceutically acceptable amine and metal salts thereof, wherein X is oxygen or divalent sulfur; A is hydrogen or lower alkyl; B is hydrogen or lower alkyl; Y is $OR_1$, $SR_1$ or

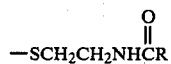

wherein $R_1$ is hydrogen or lower alkyl, and R is lower alkyl; and Z is a saturated or olefinically unsaturated hydrocarbyl moiety having 3 to 20 carbon atoms.

As used herein, the term "lower alkyl" includes the straight, branched-chain and cyclic hydrocarbyl radicals having up to 4 carbon atoms, preferably methyl, but also including ethyl, propyl, isopropyl, n-butyl, t-butyl, cyclopropyl and the like. The term "saturated or olefinically unsaturated hydrocarbyl moiety" includes those alkanyl or alkenyl moieties having 3 to 20 carbon atoms. Included within this group of compounds are those alkyl radicals such as propyl, isopropyl, n-butyl, t-butyl, dodecyl, tridecyl, tetradecyl, 3,7-dimethyloctyl, 2,4-heptadecyl, octadecyl, 3-methyloctadecyl, nonadecyl and didecyl. Included within the alkenyl radicals of this substituent are those straight and branched chain radicals having from 1 to 4 double bonds. Illustrative of this group are 9-undecenyl, 1,12-octadecadienyl, 3,7,11-trimethyl-2,6,10-octratrienyl, 8,11,14-heptadecatrienyl, 3,7-dimethyl-2,6-octadientyl, 2,4,8-decatrienyl, 3,7-dimethyl-6-octenyl. Both the cis- and the trans-isomers of the unsaturated hydrocarbyl radicals are included within the scope of this invention.

The pharmaceutically acceptable salts of the compounds of Formula (I) above include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, ethanolamines, diethanolamine, triethanolamine, N-methylglucamine, procaine, dibenzylamine, 1-ethenamine, N,N'-dibenzylethnylenediamine, dihydroabietylamine, N-(lower)alkylpiperidine, and additional amines which have been used to form non-toxic salts with benzylpenicillin. These salts can be prepared using conventional means such as containing and neutralizing a solution of the carboxylic acid in a polar solvent with a stoichiometric quantity of base.

It is apparent from the above general Formula (I) that the compounds wherein the symbol X is represented by oxygen are acylated furanyl acrylates and that the compounds are acylated thienyl acrylates when X is represented by sulfur; each group being represented by the following general Formulae II and III, respectively:

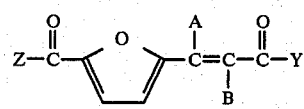   Formula II

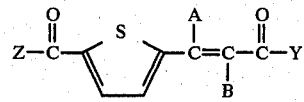   Formula III wherein Z, A, B and Y are as hereinabove defined.

In general, the compounds of this invention are prepared by standard techniques analogously known in the art wherein either a furanyl acrylate or a thienyl acrylate is subjected to an acylation reaction to produce a 5-acylated-2-furanyl acrylate or a 5-acylated-2-thienyl acrylate which, when subjected to facultative finishing steps produce the desired compounds as represented by the structures of Formulae I, II and III.

More specifically, the compounds of Formula I may be prepared by a series of chemical reactions which is initiated with a Friedel-Crafts acylation wherein a furanyl acrylate or a thienyl acrylate is reacted with a trifluoroacetyl mixed anhydride in the presence of catalytic quantities of perchloric acid to produce an ester of an appropriate 3-[5-acyl-2-furanyl]-2-propenoate or an ester of an appropriate 3-[5-acyl-2-thienyl]-2-propenoate, which esters may then be sequentially subjected to a basic hydrolysis and acidification to produce the corresponding acid (i.e., Y represents OH), which acids may be transformed to the desired amides (i.e., when Y is $NR_1R_1$) or esters (i.e., when Y is $OR_1$) or thioesters (i.e., when Y is $SR_1$ or

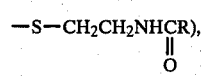

by standard techniques well-known for such transformations.

In essence, the initial Friedel-Crafts reaction may be represented by the following schematic representation

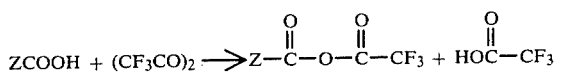

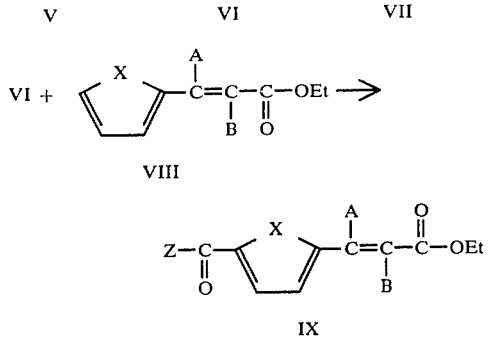

wherein the symbols Z, X, A and B are as herein defined.

In effecting this acylation reaction, a trifluoroacetyl mixed anhydride is formed, in situ, by admixing the appropriate saturated straight- or branched-chain monocarboxylic acid or unsaturated (mono-, di-, tri- or tetraolefinic) straight or branched chain monocarboxylic acids (IV) with trifluoroacetic anhydride (V) at room temperature. The mixed anhydride is then reacted with the acrylate (VIII) in the presence of catalytic quantities of perchloric acid. The Friedel-Crafts acylation is conducted by admixing molar equivalent quantities of the reactants at temperatures of about −40° C. to about room temperature in the presence of catalytic quantities (up to 0.1 molar) of perchloric acid, preferably in the form of a 70% aqueous solution. The reaction may be conducted with or without a non-reactive solvent standard for this reaction (e.g., ether, methylene chloride, benzene, nitrobenzene or other known Friedel-Crafts solvents). The so-obtained alkyl 3-[5-acyl-2-furanyl]-2-propenoates or 3-[5-acyl-2-thienyl]-2-propenoates are then converted to their free acids for further conversion to their salts, esters, amides and thioesters according to techniques well known in the art.

Alternatively, the compounds of Formula III also may be prepared by a series of chemical reactions which is initiated with a Friedel-Crafts acylation procedure. This acylation utilizes standard procedures wherein the appropriate acid, in the form of its acid chloride derivative, is reacted with an alkyl 3-(2-thienyl)-acrylate, said acylation being done in the presence of a catalyst according to the following schematic representation:

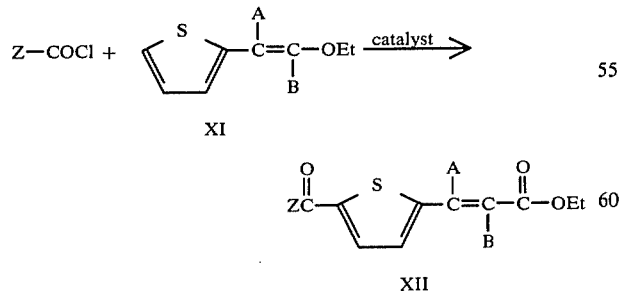

In effecting the foregoing, the appropriate acid (IV) is first converted to its acid chloride by reaction of the acid with thionyl chloride according to standard procedures. The acid chloride is then subjected to the Friedel-Crafts reaction with the ethyl ester of thienyl acrylate wherein equimolar amounts of the reactants are stirred at temperatures of about −20° C. to about room temperature for about ½ to 4 hours and then heated to reflux until the reaction is complete, usually about 5 to 20 minutes. The reaction takes place in the presence of such standard Friedel-Crafts catalysts as, for example, ferric chloride and stannic chloride. Here too, the acylation may optionally take place in the presence of a non-reactive solvent usually utilized for such reactions. Conversion of the so-obtained alkyl 3-[5-acyl-2-thienyl]-acrylate (XII) to the desired acid by basic hydrolysis and neutralization techniques, which acid may then be transformed to the desired amides, esters or thioesters by standard techniques.

Exemplary of the facultative finishing steps for obtention of the desired amides, esters and thioesters are: (a) reaction of the acid chloride forms of compound IX with N-acetylcysteamine or other thiols (i.e., $HSR_1$) or ROH according to standard techniques will produce the desired thioesters, (b) reaction of the said chloride form of compound IX with strong ammonium hydroxide in a non-reactive solvent (e.g., tetrahydrofuran) will give the corresponding amide, (c) reaction of compounds IX and XII with the appropriate amine (e.g., diethylamine) according to standard techniques will give the desired alkenamide, and (d) esterification of the acid forms of compound VIII with the appropriate alcohol will yield the desired esters. Such reactions may generally be depicted by the following schematic representations.

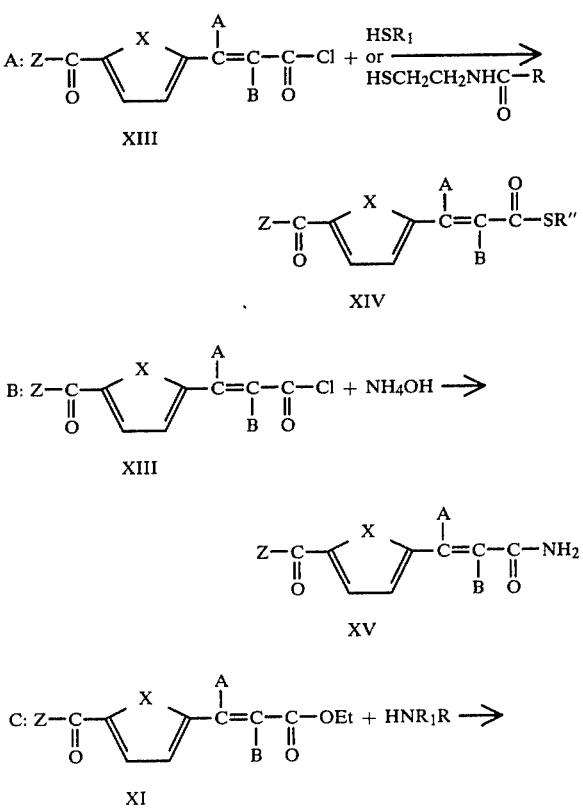

-continued

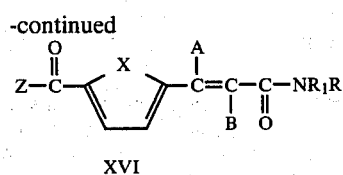

XVI

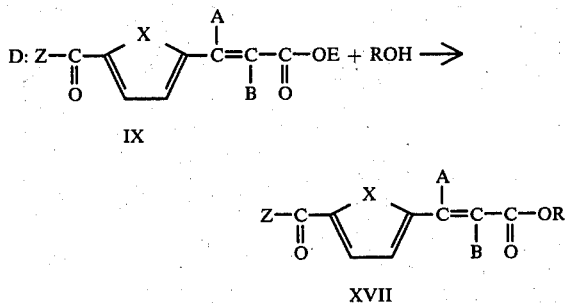

IX

XVII wherein the above Z, A, B, R and $R_1$ symbols are as previously defined and R'' is $R_1$ or

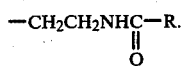

The following examples are illustrative of the techniques and procedures for preparing the compounds of this invention.

EXAMPLE 1

Ethyl (E)-3-[5-(1-oxododecyl)-2-furanyl]-2-propenoate

A mixture of 11.8 g (0.0589 mole) of lauric acid and 14.8 g (0.0707 mole) of trifluoroacetic anhydride is stirred at room temperature for ½ hour. To the mixture 10.0 g (0.060 mole) of ethyl-2-furanylacrylate is added and the mixture is cooled to about −10° C. One ml of 70% perchloric acid is added and the mixture is warmed to room temperature and stirred for 1 hour. The mixture is diluted with 100 ml of ether and treated with saturated aqueous $Na_2CO_3$ until basic. The layers are separated and the ether layer washed with saturated aqueous $Na_2CO_3$, water, brine and then evaporated to dryness. The residue is distilled 160°–190° C. (0.1 mm Hg) to give ethyl (E)-3-[5-(1-oxododecyl)-2-furanyl]-2-propenoate, mp 50°–51° C.

In a similar manner, by substitution of the lauric acid used in this example with equivalent quantities of the following acids and by following substantially the same procedure, there are produced the corresponding ethyl (E)-3-[5-(1-oxo-Z)-2-furanyl]-2-propenoate: n-butyric acid, n-valeric acid, iso-butyric acid, iso-valeric acid, caporic acid, enanthic acid, caprylic acid, pelargonic acid, capric acid, undecylic acid, tridecylic acid, myristic acid, pentadecylic acid, palmitic acid, margaric acid, stearic acid, mondecylic acid, arachidic acid, crotonic acid (cis and trans), $\Delta^2$-hexenoic acid, $\Delta^4$-decenoic acid, $\Delta^9$-decenoic acid, linderic acid, lauroleic acid, $\Delta^9$-dodenoic, $\Delta^4$-tetradeconic acid, physeteric acid, myristoleic acid, palmitoleic acid, petroselinic acid, oleic acid, elidoic acid, vaccenic acid, $\Delta^{12}$-octadecenoic acid, gadoleic acid, $\Delta^{11}$-eicosenoic acid, cetoleic acid, sorbic acid, linoleic acid, hirogonic acid, eleosteraic acid, linolenic acid, stearidonic acid, timnodonic acid, arachidonic acid and tuberculostearic acid.

Similarly, by substituting the ethyl 2-furanylacrylate with equivalent quantities and by reacting that reactant with equivalent quantities of all of the foregoing acids by following substantially the same procedure there is produced the corresponding ethyl (E)-3-[5-(1-oxo-Z)-2-thienyl]-2-propenoate.

EXAMPLE 2

(E)-3-[5-(1-oxododecyl)-2-furanyl]-2-propenoic acid

A mixture of 5.0 g (0.014 mole) of ethyl (E)-3-[5-(1-oxododecyl)-2-furanyl]-2-propenoate and 108 ml of ethanol, is heated to reflux. To the mixture is added 50 ml of 1 N aqueous sodium hydroxide, the ethanol is distilled off being replaced with water, and the aqueous solution is cooled to room temperature acidified with 200 ml of 1 N hydrochloric acid. The solid is collected by filtration and dried. Recrystallization from methanol gives (E)-3-[5-(1-oxododecyl)-2-furanyl]-2-propenoic acid, mp 122°–127° C.

Similarly, by substituting equivalent quantities of all of those esters produced in Example 1, and by substantially following the hydrolysis/acidification procedures of this example, the corresponding 3-[5-(1-oxo-Z)-2-furanyl]-2-propenoic acids and 3-[5-(1-oxo-Z)-2-thienyl]-2-propenoic acids are produced.

EXAMPLE 3

Ethyl 2-methyl-3-[5-(1-oxo-3,7,11-trimethyldodecyl)-2-furanyl]-2-propenoate

A mixture of 24.2 g (0.1 mole) of 3,7,11-trimethyl-dodecanoic acid and 21.0 g (0.1 mole) of trifluoroacetic anhydride is stirred at reflux for ½ hour. The mixture is cooled and 18.0 g (0.1 mole) of ethyl 3-(2-furanyl)-2-methylpropenoate is added. The mixture is cooled to about 0° C. and 5 drops of 70% perchloric acid is added. The mixture is stirred at 0° C. for 2 hours, then diluted with anhydrous ether and treated with saturated aqueous sodium carbonate solution until basic. The layers are separated and the ether layer washed with water, brine and evaporated to dryness. The residue is distilled at reduced pressure to give ethyl 2-methyl-3-[5-(1-oxo-3,-7,11-trimethyldodecyl)-2-furanyl]-2-propenoate.

EXAMPLE 4

S-[2-(acetylamino)ethyl]2-methyl-3-[5-(3,7,11-trimethyl-1-oxo-dodecyl)-2-furanyl]-2-propenthioate Part 1

A mixture of ethyl-2-methyl-3-[5-(1-oxo-3,7,11-trimethyldodecyl)-2-furanyl]-2-propenoate (20.2 g–0.05 mole) in 200 ml ethanol is heated to reflux, 100 ml of 1 N aqueous NaOH is added and the mixture is refluxed for 2 hours, cooled, diluted with water, acidified with 200 ml 1 N aqueous hydrochloric acid and extracted with ether. The ether layer is evaporated to dryness to give 2-methyl-3-[5-(1-oxo-3,7,11-trimethyldodecyl)-2-furanyl]-2-propenoic acid.

Part 2

The foregoing acid is added to a mixture of 6.9 g (0.6 mole) of α,α-dichloromethyl methyl ether in 50 ml of dichloromethane. The mixture is stirred at room temperature overnight, then evaporated to dryness under reduced pressure to give the corresponding acid chloride.

Part 3

A mixture of 15.0 g (0.038 mole) of 2-methyl-3-[5-(1-oxo-3,7,11-trimethyldodecyl)-2-furanyl]-2-propenoyl chloride and 4.8 g (0.04 mole) of N-acetyl cysteamine, and 5.5 g of potassium carbonate in 200 ml of anhydrous ether is stirred at room temperature overnight. The mixture is filtered and the filtrate evaporated to dryness to give S-[2-(acetylamino)ethyl]2-methyl-3-[5-(3,7,11-trimethyl-1-oxo-dodecyl)-2-furanyl]-2-propenthioate.

In a similar manner, all of those acids produced by the process of Example 2 may be converted to the corresponding acid chloride by following part 2 of this example, and the so-obtained acid chlorides may then be converted to the corresponding thioester by following the procedure of part 3 of this example.

EXAMPLE 5

3-[5-(cycloheptadecylacetyl)-2-thienyl]-2-propenamide

A mixture of 29.6 g (0.1 mole) of cycloheptadecyl acetic acid and 35.7 g (0.3 mole) of thionyl chloride in 300 ml of toluene is heated to reflux for 4 hours, the mixture is evaporated to dryness under reduced pressure to give the corresponding acid chloride. The above acid chloride is added to 18.2 g (0.1 mole) of ethyl 3-(2-thienyl)acrylate. The mixture is cooled to about $-10°$ C. and 78.2 g (0.3 mole) of stannic chloride is slowly added with stirring. The reaction is allowed to warm to room temperature for 2 hours, then heated to reflux for 15 minutes. The mixture is cooled and poured into an ice-10% aqueous hydrochloric acid mixture. Ether is added and the layers separated. The ether layer is washed with 1 N aqueous hydrochloric acid, water, saturated sodium carbonate solution, brine and evaporated to dryness. The residue is distilled under high vacuum to give ethyl 3-[5-(cycloheptadecylacetyl)-2-thienyl]-2-propenoate.

A mixture of 23.0 g (0.05 mole) of the above ester and 250 ml of ethanol are heated to reflux, 100 ml of 1 N aqueous sodium hydroxide is added and the mixture refluxed for 3 hours, then cooled to room temperature. The mixture is acidified to pH 1 with 1 N hydrochloric acid, ether is added and the layers separated. The ether layer is washed with water and evaporated to dryness to give 3-[5-(cycloheptadecylacetyl)-2-thienyl]-2-propenoic acid. This acid is added to 6.9 g (0.06 mole) of $\alpha,\alpha$-dichloromethyl methyl ether in 100 ml of dichloromethane. The mixture is refluxed overnight then evaporated to dryness to give the corresponding acid chloride which is added to 200 ml of tetrahydrofuran. To the above mixture is added 100 ml of strong ammonium hydroxide solution. The mixture is stirred overnight, is diluted with 500 ml of water and filtered. The precipitate is washed with water and dried to give 3-[5-(cycloheptadecylacetyl)-2-thienyl]-2-propenamide.

In a similar manner, all of those esters prepared by the process of Example 1 may also be converted to the corresponding acids and chlorides, and thence to the corresponding amides by following the teaching of this example.

EXAMPLE 6

N,N-diethyl-3-[5-(1-oxo-9,12,15-octadecatrienyl)-2-furanyl]-2-butenamide

A mixture of 13.0 g (0.05 mole) of linolenic acid and 12.6 g (0.06 mole) of trifluoroacetic anhydride is stirred at room temperature for 1 hour. To the mixture 9.0 g (0.05 mole) of ethyl 3-(2-furanyl)-2-butenoate is added and the mixture is cooled and stirred at $-10°$ C. To the mixture 5 drops of 70% perchloric acid is added and the mixture stirred at 0° C. for 3 hours. The mixture is diluted with 200 ml of ether and combined with 200 ml of saturated aqueous sodium carbonate. The layers are separated and the ether layer is washed with water, brine and evaporated to dryness. The residue is distilled under high vacuum to give ether 3-[5-(1-oxo-9,12,15-octadecatrienyl)-2-furanyl]-2-butenoate, which ester is dissolved in 300 ml of anhydrous ethanol and the solution is cooled on an ice-bath. To the mixture 14.6 g (0.2 mole) of diethylamine is added and the mixture allowed to warm up to room temperature and stand for 3 days. The reaction mixture is evaporated to dryness to give N,N-diethyl-3-[5-(1-oxo-9,12,14-octadecatrienyl)-2-furanyl]-2-butenamide.

Similarly, by following the teaching of this example, corresponding amides may be prepared for each of those compounds prepared by example 1.

EXAMPLE 7

Isopropyl (E)-3-[5-(1-oxodocecyl)-2-furanyl]-2-propenoate

A mixture of 5.0 g (0.0156 mole) of (E)-3-[5-(1-oxododecyl)-2-furanyl]-2-propenoic acid and 10 ml of $\alpha,\alpha$-dichloromethyl methylether is heated on a steam bath for 2 hours, then evaporated to dryness under reduced pressure to give (E)-3-[5-(1-oxododecyl)-2-furanyl]-2-propenoyl chloride.

A mixture of 5.3 g of the above acid chloride and 100 ml of isopropanol are stirred at room temperature for 2 hours, then evaporated to dryness to give isopropyl (E)-3-[5-(1-oxododecyl)-2-furanyl]-2-propenoate.

EXAMPLE 8

Potassium (E)-3-[5-(1-oxododecyl)-2-furanyl]-2-propenoate

A mixture of 5.0 g (0.0156 mole) of (E)-3-[5-(1-oxododecyl)-2-furanyl]-2-propenoic acid, 1.0 g of potassium hydroxide and 100 ml of methanol is heated with stirring on a steam bath for 1 hour. The methanol is distilled off to 50 ml and the mixture cooled. The solid is separated by filtration to give potassium (E)-3-[5-(1-oxododecyl)-2-furanyl]-2-propenoate, m.p. 220°–230° C. (decomposition).

EXAMPLE 9

Ammonium (E)-3-[5-(1-oxododecyl)-2-furanyl]-2-propenoate

A mixture of 5.0 g (0.0156 mole) of (E)-3-[5-(1-oxododecyl)-2-furanyl]-2-propenoic acid and 200 ml of anhydrous ether is stirred at room temperature. The above mixture is saturated with ammonia gas and allowed to stand at room temperature overnight. The solid precipitate is separated by filtration and washed with ether to give ammonium (E)-3-[5-(1-oxododecyl)-2-furanyl]-2-propenoate.

The compounds described herein are useful as hypolipidemic agents in that they reduce blood lipids, particularly cholesterol and triglycerides without concurrent accumulation of desmosterol. These compounds can be administered to animals, mammals, rats, cats, dogs, cattle, horses and humans, and can be useful in the treatment of hyperlipidemic states such as are encountered in patients with cardiovascular diseases that can result in heart failure and stroke. As used herein, the term patient is intended to mean the animal or mammal being treated.

The utility of the compounds disclosed herein may be demonstrated in young male rats of the Wistar strain initially weighing about 175 grams which are given free excess to a diet containing 0.15 percent by weight of test compound, that is, a compound of general Formula I. This diet is prepared by mixing the test compound with commercial Purina Chow. (Trade Mark of Ralston-Purina Company, St. Louis, Missouri.) Groups of animals are given these diets for either 4 to 10 days. Control groups of 6 rats each are given Purina Chow to which no test compound has been added. At the end of the treatment, all rats are bled by cardiac puncture, and the plasma is analyzed for cholesterol and triglyceride content. Analogously, the compounds of this invention may also be tested utilizing the Triton-Mouse.

The compounds of this invention can be administered orally or parenterally either alone or in the form of pharmaceutical preparations. Pharmaceutical preparations containing conventional pharmaceutical carriers and the active-ingredients compounds of this invention can be employed in unit dosage form such as solids, for example, tablets, capsules and pills or liquid solutions, suspensions or emulsions for oral and parenteral administration. The dosage unit administered can be any lipid lowering effective amount. The quantity of the compound administered can vary over a wide range to provide from about 0.5 mg/kg (milligram per kilogram) to about 150 mg/kg of body weight of the patient per day, and preferably, from about 10 mg/kg to 30 mg/kg of body weight of the patient per day, to achieve the desired effect. Unit doses can contain from about 50 mg to 1 g (gram) of a compound described herein and may be administered, for example, from 1 to 4 times daily. Illustrative examples of pharmaceutical preparations of the compounds described herein are the following.

An illustrative composition for tablets is as follows:

|  | Per Tablet |
|---|---|
| (a) (E)-3-[5-(1-oxododecyl)-2-furanyl]-2-propenoic acid | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following wherein the quantities are on a weight to volume basis.

|  | Amount |
|---|---|
| (a) (E)-3-[5-(1-oxododecyl)-2-furanyl]-2-propenoic acid | 100.0 mg |
| (b) peanut oil | 1.0 ml |

The active ingredient is suspended in the oil and to the suspension is added an appropriate amount of a preservative such as methylparaben or propylparaben.

An illustrative composition for hard gelatin capsules is as follows:

|  | Amount |
|---|---|
| (a) (E)-3-[5-(1-oxododecyl)-2-furanyl]-3-propenoic acid | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsules.

An illustrative composition for pills is the following:

|  | Per Pill |
|---|---|
| (a) (E)-3-[5-(1-oxododecyl)-2-furanyl]-2-propenoic acid | 200 mg |
| (b) corn starch | 130 mg |
| (c) liquid glucose | 20 ml |

The pills are formed by blending the active ingredient (a) and the corn starch and then adding the liquid glucose with thorough kneading to form a plastic mass from which the pills are cut and formed.

As is true for most classes of therapeutically effective compounds, certain sub-classes are found to be more effective than others. In this instance, those compounds wherein "X" is oxygen are preferred over their sulfur analogs. Another preferred sub-class are those wherein "A" and "B" are hydrogen. Another preferred sub-class are those compounds wherein "Z" represents a moiety having 7 to 12 carbon atoms. Another preferred sub-class are those compounds where "Z" is a saturated hydrocarbyl moiety with those compounds bearing double-bonds being next preferred. Another preferred sub-class of compounds are those wherein "Y" is "$OR_1$" or "$-SCH_2CH_2NHCOR$".

I claim:

1. A compound of the structural formula $$Z-\overset{O}{\overset{\|}{C}}-\underset{}{\boxed{\phantom{XX}X\phantom{XX}}}-\overset{A}{\underset{B}{C}}=C-\overset{O}{\overset{\|}{C}}-Y$$

and the pharmaceutically acceptable amine and metal salts thereof, wherein

X is oxygen or a divalent sulfur atom;
A is hydrogen or lower alkyl;
B is hydrogen or lower alkyl;
Y is $OR_1$, $NR_1R_1$, $SR_1$ or $-SCH_2CH_2NHCOR$ wherein $R_1$ is hydrogen or lower alkyl and R is lower alkyl; and
Z is a saturated or olefinically unsaturated hydrocarbyl moiety having 3 to 20 carbon atoms.

2. A compound of claim 1 wherein X is oxygen.

3. A compound of claim 1 wherein X is a divalent sulfur atom.

4. A compound of claim 2 wherein Y is $OR_1$.

5. A compound of claim 2 wherein Y is $-SCH_2CH_2NHCOR$.

6. A compound of claim 2 wherein Z is $n-C_{11}H_{23}$, A and B are each hydrogen and Y is OH, said compound being (E)-3-[5-(1-oxododecyl)-2-furanyl]-2-propenoic acid.

7. A compound of claim 2 wherein Z is $n-C_{11}H_{23}$, A and B are each hydrogen and Y is O-ethyl, said compound being ethyl (E)-3-[5-(1-oxododecyl)-2-furanyl]-2-propenoate.

8. A method of reducing the lipid concentration in the blood of a patient in need thereof which comprises administering to said patient a lipid-lowering effective amount of a compound of claim 1.

* * * * *